United States Patent
Andersen et al.

(10) Patent No.: US 10,617,564 B1
(45) Date of Patent: Apr. 14, 2020

(54) AREA SCANNING PHOTOMEDICINE DEVICE AND METHOD

(75) Inventors: Dan Andersen, Menlo Park, CA (US); David Mordaunt, Los Gatos, CA (US)

(73) Assignee: Apple Inc., Cupertino, CA (US)

(*) Notice: Subject to any disclaimer, the term of this patent is extended or adjusted under 35 U.S.C. 154(b) by 2651 days.

(21) Appl. No.: 11/800,939

(22) Filed: May 7, 2007

Related U.S. Application Data

(60) Provisional application No. 60/799,517, filed on May 10, 2006.

(51) Int. Cl.
*A61F 9/008* (2006.01)

(52) U.S. Cl.
CPC .......... *A61F 9/008* (2013.01); *A61F 9/00821* (2013.01); *A61F 2009/00897* (2013.01)

(58) Field of Classification Search
CPC .... A61B 3/12–145; A61F 9/007; A61F 9/008; A61F 9/00821; A61F 2009/00861–00876; A61F 2009/00897; A61F 9/00; A61F 9/00802; A61F 9/00825; A61F 2009/00863; A61F 2009/00885; G06T 2207/30041; A61N 5/06; A61N 5/0613; A61N 5/0622; A61N 2005/0626; A61N 2005/0627; A61N 2005/0642; A61N 2005/067
USPC ............ 606/4–6, 9–13; 607/88, 89; 128/898
See application file for complete search history.

(56) References Cited

U.S. PATENT DOCUMENTS

| | | |
|---|---|---|
| 4,538,299 A | 8/1985 | De Forest |
| 4,884,884 A | 12/1989 | Reis |
| 4,907,586 A * | 3/1990 | Bille et al. ................ 606/5 |
| 4,917,486 A | 4/1990 | Raven et al. |
| 5,391,165 A | 2/1995 | Fountain et al. |
| 5,425,729 A | 6/1995 | Ishida et al. |
| 5,480,396 A | 1/1996 | Simon et al. |
| 5,514,127 A | 5/1996 | Shanks |
| 5,543,866 A | 8/1996 | Van De Velde |
| 5,568,208 A | 10/1996 | Van De Velde |

(Continued)

FOREIGN PATENT DOCUMENTS

WO     WO 2005/065116     * 7/2005     ............. A61F 9/008

OTHER PUBLICATIONS

Naess et al., "Computer-Assisted Laser Photocoagulation of the Retina-a Hybrid Tracking Approach", *Journal of Biomedical Optics*, Apr. 2002, vol. 7, No. 2, pp. 179-189.

(Continued)

*Primary Examiner* — Ahmed M Farah
(74) *Attorney, Agent, or Firm* — Dentons US LLP

(57) ABSTRACT

A system and method for treating a lesion on target tissue that includes a visualization device for capturing an image of target tissue containing a lesion, a light source for generating a light beam, a scanner for deflecting the light beam in the form of a treatment pattern, and a controller for determining boundaries of the lesion from the captured image, and for controlling the scanner to project the treatment pattern onto the target tissue and within the boundaries of the lesion. An alignment light source can be used to generate an alignment light beam, such that the scanner deflects the alignment light beam in the form of an alignment pattern. The controller controls the scanner to project the alignment pattern onto the target tissue to visually indicate a position of the treatment pattern on the target tissue.

18 Claims, 14 Drawing Sheets

(56) References Cited

U.S. PATENT DOCUMENTS

| | | | |
|---|---|---|---|
| 5,625,709 A | 4/1997 | Kasdan | |
| 5,743,902 A | 4/1998 | Trost | |
| 5,748,352 A | 5/1998 | Hattori | |
| 5,892,569 A | 4/1999 | Van de Velde | |
| 5,943,117 A | 8/1999 | Van de Velde | |
| 5,957,915 A | 9/1999 | Trost | |
| 5,971,978 A | 10/1999 | Mukai | |
| 5,980,513 A | 11/1999 | Frey et al. | |
| 6,011,563 A | 1/2000 | Fournier | |
| 6,033,396 A * | 3/2000 | Huang et al. | 606/5 |
| 6,066,128 A | 5/2000 | Bahmanyar et al. | |
| 6,096,028 A | 8/2000 | Bahmanyar et al. | |
| 6,099,522 A * | 8/2000 | Knopp et al. | 606/10 |
| 6,149,644 A | 11/2000 | Xie | |
| 6,186,628 B1 | 2/2001 | Van de Velde | |
| 6,267,756 B1 | 7/2001 | Feuerstein et al. | |
| 6,328,733 B1 | 12/2001 | Trost | |
| 6,347,244 B1 | 1/2002 | Dubnack | |
| 6,494,878 B1 * | 12/2002 | Pawlowski | A61F 9/008 606/4 |
| 6,705,726 B2 | 3/2004 | Tanassi et al. | |
| 6,789,900 B2 * | 9/2004 | Van de Velde | A61F 9/008 351/221 |
| 6,984,228 B2 * | 1/2006 | Anderson | A61N 5/0616 606/12 |
| 7,115,120 B2 * | 10/2006 | Lin | A61F 9/008 606/4 |
| 7,146,983 B1 | 12/2006 | Hohla et al. | |
| 7,418,169 B2 * | 8/2008 | Tearney | A61B 1/00082 606/7 |
| 7,583,827 B2 * | 9/2009 | Hansen | G06T 7/0012 382/128 |
| 10,179,071 B2 * | 1/2019 | Mordaunt | A61F 9/008 |
| 2002/0133144 A1 * | 9/2002 | Chan | A61F 9/008 606/4 |
| 2006/0100677 A1 | 5/2006 | Blumenkranz et al. | |

OTHER PUBLICATIONS

Markow et al., "An Automated Laser System for Eye Surgery", *IEEE Engineering in Medicine and Biology Magazine*, Dec. 1989, pp. 24-29.

Wright et al., "Hybrid Approach to Retinal Tracking and Laser Aiming for Photocoagulation", *Journal of Biomedical Optics*, Apr. 1997, vol. 2 No. 2, pp. 195-203.

Barrett et al., "Computer-Aided Retinal Photocoagulation System", *Journal of Biomedical Optics*, Jan. 1996, vol. 1 No. 1, pp. 83-91.

Van de Velde, "Role of the Scanning Laser Ophthalmoscope in Photodynamic Therapy of Macular Disease", *Ophthalmic Technologies X, Proceedings of SPIE*, vol. 3908 (2000)pp. 190-201.

Barrett et al., "Digital Imaging-Based Retinal Photocoagulation System", *SPIE*, vol. 2971 pp. 118-128.

Wright et al., "Initial In Vivo Results of a Hybrid Retinal Photocoagulation System", *Journal of Biomedical Optics*, Jan. 2000, vol. 5 No. 1, pp. 56-61.

* cited by examiner

AREA SCANNING PHOTOMEDICINE DEVICE AND METHOD

This application claims the benefit of U.S. Provisional Application No. 60/799,517, filed May 10, 2006.

FIELD OF THE INVENTION

The present invention relates to therapeutic photomedicine devices and methods, and more particularly to a multipurpose scanning photomedicine system and method for use in the treatment of lesions (including precancerous and cancerous), especially ideal for use in ophthalmology, dermatology, gynecology, gastroenterology, and thoracic surgery.

BACKGROUND OF THE INVENTION

There have been many recent advances in the area of photomedicine for the treatment of superficial lesions, including treatment of precancerous and cancerous lesions using photocoagulation (PC), thermotherapy (TT), and photodynamic therapy (PDT). These three types of treatment utilize very different mechanisms, but all involve administering light to the target tissue to affect therapy. The term superficial lesion is understood here to mean that the lesion is on or near the surface of target tissue and thereby accessible to light that is administered to the target tissue surface. For example, in ophthalmology, all three treatment approaches are being used in the treatment of age-related macular degeneration (ARMD), a leading cause of irreversible visual loss. Likewise, in dermatology, PDT is presently being used to treat melanoma, non-melanoma, actinic keratoses, as well as both basal and squamous cell carcinomas. PC is presently being used to remove vascularities. Other areas of treatment that can benefit from the above listed approaches include, but are not limited to, gynecology, gastroenterology, and thoracic surgery. Although the details of the approaches vary due to the anatomical differences presented, the fundamental underpinnings are the same. That is, one must provide treatment light to the targeted lesion. To date, this has been done primarily with broad-brush application of light to the lesion and its surrounding tissue. While this has the advantage of being straightforward, it also limits the ultimate clinical efficacy by increasing the side effect profile. This is because these therapies are not sufficiently site selective in their efforts. The irradiation of adjacent tissue causes more damage than is necessary. Therefore, a more selective approach to delivering therapeutic light to lesions is needed, which minimizes the irradiation of adjacent, non-targeted tissue.

The light sources used for these different therapies may be continuous wave (cw) where the light is produced and delivered in a continuous, uninterrupted manner, or quasi-cw which is where the light is modulated at a pulse repetition frequency (PRF) too high to be distinguished from cw light in terms of its effect on the target tissue (for the purposes of this disclosure at or above 2 KHz). Examples of the three major photomedical therapies mentioned above are now described in more detail below.

1. Photocoagulation

Retinal photocoagulation may be performed at a variety of wavelengths. The light need only be primarily absorbed by the targeted chromophore, and not its surroundings. The targeted chromophore is often the melanin resident in the retinal pigment epithelium (RPE). Retinal photocoagulation is typically performed using green light, because of melanin's high absorption of light in this wavelength range. However, blood strongly absorbs light below 600 nm. To accommodate this, longer wavelength light is often used when blood is present in the aqueous humor. FIG. 1 shows the optical absorption properties of the predominant autogenous ocular chromophores; namely melanin in the RPE, oxy-hemoglobin ($HbO_2$), and deoxy-hemoglobin (Hb), as compared to epidermis. The successful clinical use of red light to affect photocoagulation by targeting melanin has been well established using both 647 & 810 nm light from Krypton ion & semiconductor lasers, respectively. The choices of these wavelengths has been historically based upon the availability of light sources at these wavelengths, and not necessarily by the spectroscopic properties of the target tissue. Because of the monotonic character of melanin's optical absorption, and the lack of sufficient absorption in blood or water, red light photocoagulation can be effectively performed with light within the range of 600-900 nm.

2. Thermotherapy

In the context of ophthalmology, transpupillary thermotherapy (TT) is the slow heating of the subfoveal choroidal neovascular complex to occlude CNV (Choridal Neovascularization). An 810 nm laser diode system has been used as the light source, where the light is delivered in a large single round spot that covers the entire treatment complex. With properly selected small choroidal melanomas, tumor control has proven to be excellent. The heat induces cellular damage at the site of treatment with few remote side effects. However there are often complications adjacent to the site of treatment, including retinal vascular obstruction, and retinal traction.

3. Photodynamic Therapy

Photodynamic Therapy (PDT) is currently practiced by injecting a photoactivation drug that specifically binds to diseased tissues, and is sensitive to certain wavelengths of light for subsequent photoactivation to produce highly reactive byproducts, such as singlet oxygen. After injecting a photoactivation drug, a physician then typically irradiates a portion of the tissue that is considerably larger than necessary for a period sufficient to realize the therapeutic photochemistry. This broad-brush approach generally tends to minimize the losses due to optical scattering. However, with the relatively long wavelengths used for PDT, optical scattering is less of a concern than it is for other therapies. Below is a table of photoactivation drugs and their excitation wavelengths that have been used in PDT:

| Photoactivation Drug | $\lambda$ [nm] |
|---|---|
| DHE | 630 |
| HP | 630 |
| HpD | 630 |
| PF | 630 |
| PpIX | 630 |
| Chle6 | 662 |
| SnET2 | 664 |
| ATXSI0 | 670 |
| AlS4Pc | 673 |
| CASPc | 675 |
| BPDMA | 690 |
| LuTex | 732 |
| Bacteriochlorina | 760 |
| SINc | 779 |

PDT has been used to treat a variety of conditions, such as Barrett's esophagus, esophageal adenocarcinoma, uveal melanoma, retinoblastoma, choroidal neovascularization, melanoma, non-melanoma, actinic keratoses, and both basal and squamous cell carcinomas. However, PDT has yet to be optimized. Today, physicians typically treat their PDT patients by adhering to a rigid protocol under which the laser spot size, treatment time, and laser power are all fixed. Although there have been feedback mechanisms proposed for PDT, none are known to have been clinically implemented. Such feedback mechanisms would only improve the overall effectiveness of any approach.

Because photoactivation drugs used are not perfectly selective, PDT can cause damage to adjacent healthy tissue. A measure of this selectivity is the "retention ratio," a value defined as the ratio between the photoactivation drug concentration in diseased tissue to that of the adjacent normal tissue. Typical retention ratio values ranging from 2 to 5 have been reported. Therefore, some amount of healthy tissue immediately surrounding the targeted lesion tissue must be sacrificed to assure that the entire population of diseased cells has been eradicated. However, as illustrated in FIG. 2, the irradiation geometry of the applied light 1 is typically circular, while the lesions 2 generally are not circular. Thus, the drug's imperfect retention ratio and the light source's large, circular spot together create relatively large amounts of unwanted cellular damage adjacent to the target lesion.

One attempt to reduce adjacent tissue damage has been to scan the light beam across the lesion in a pattern that generally covers the surface area of the lesion. For example, a discontinuous raster scan pattern has be used to sweep the beam across the lesion in successive rows. However, such scans have been performed in simple geometries (such as squares and hexagons) which again bear little relation to the arbitrary shape of the lesion. Such scans also include excessive numbers of discontinuities between multiple scans adding inefficiency and possible sources of error to the treatment.

SUMMARY OF THE INVENTION

The present invention solves the aforementioned problems by providing a multipurpose system for performing a variety of photomedical procedures that is based on contiguous scanning of a continuous wave (cw) or quasi-cw light source. The system has direct implications for standard photocoagulation (PC), photodynamic therapy (PDT), thermotherapy (TT). Unlike other approaches, the present invention allows for spatially contained and uniform energy deposition, or creating tailored temperature profiles and customized therapy for cancerous and precancerous lesions, where the treatment is better limited to the lesion itself as opposed to surrounding tissue.

A device for treating a lesion on target tissue includes a visualization device for capturing an image of target tissue containing a lesion, a light source for generating a light beam, a scanner for deflecting the light beam in the form of a treatment pattern, and a controller for determining boundaries of the lesion from the captured image, and for controlling the scanner to project the treatment pattern onto the target tissue and within the boundaries of the lesion.

A method for treating a lesion on target tissue includes capturing an image of target tissue containing a lesion, generating a light beam, deflecting the light beam in the form of a treatment pattern, determining boundaries of the lesion from the captured image, and projecting the treatment pattern onto the target tissue and within the boundaries of the lesion.

Other objects and features of the present invention will become apparent by a review of the specification, claims and appended figures.

DETAILED DESCRIPTION OF THE PREFERRED EMBODIMENTS

The present invention provides a system and method for treating lesions with light where the boundaries of the lesions are identified such that the patterns of treatment light scanned onto the legions are better limited to regions of the legions within the identified boundaries. The system and method are ideal for photocoagulation (PC), thermotherapy (TT), and photodynamic therapy (PDT).

Figure 1:
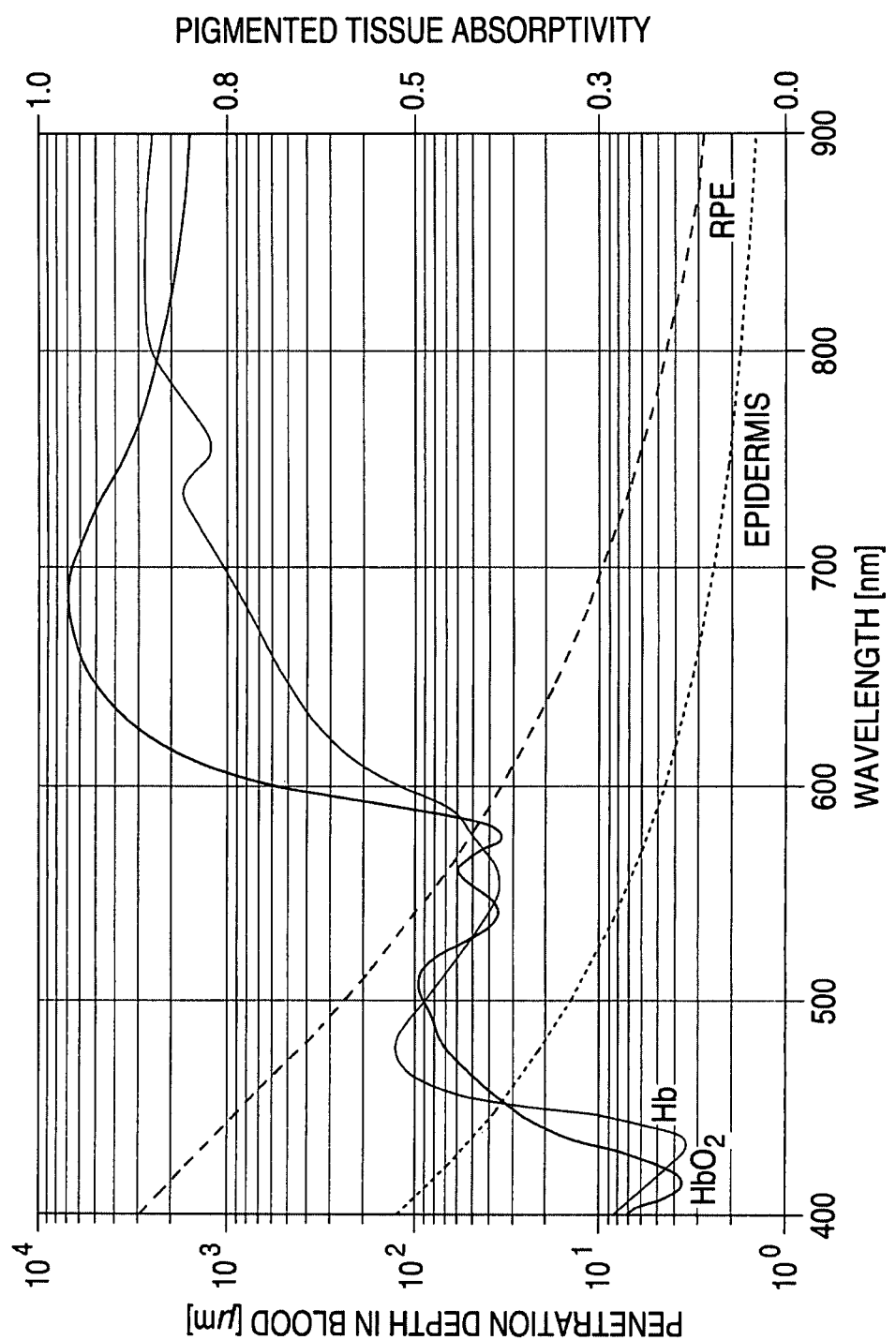
FIG. 1 is a graph illustrating the optical absorption characteristics of the predominant chromophores such as melanin (in RPE), oxy-hemoglobin (HbO2), and deoxy-hemoglobin (Hb).
Figure 2:
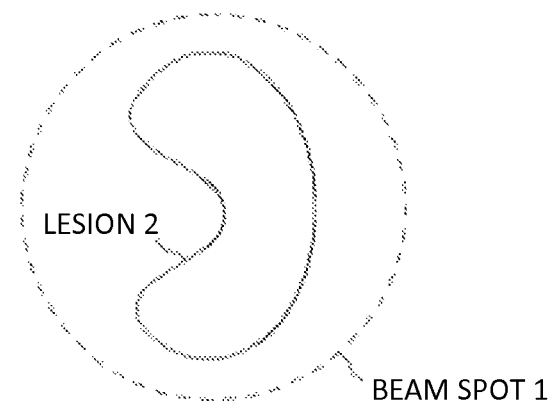
FIG. 2 is a schematic representation illustrating the difference in geometry between a lesion and a conventional circular treatment beam spot applied to the lesion.

As discussed above, FIG. 1 shows the optical absorption characteristics of typically encountered chromophores: melanin (found in RPE), oxy-hemoglobin (HbO$_2$), and deoxy-hemoglobin (Hb). The optical penetration depths of the hemoglobin chromophores are shown using the left-hand abscissa, and the single-pass absorptivities for the RPE and Epidermis are shown using the right-hand abscissa. The pigmented tissues' absorption spectra, $A_i$, were modeled using the relation $A_i = 1 - e^{-dv_f/\mu_a}$ where d is the tissue thickness, $v_f$ is the volume fraction of melanosomes within the tissue, $\mu_a$ is the individual melanosome absorption coefficient expressed as $\mu_a = (K\lambda^{3.48})*10^{12}$, and $\lambda$ is the wavelength expressed in nanometers. Specific values for the RPE and Epidermis are given below:

| Tissue | d [µm] | $v_f$ | K |
|---|---|---|---|
| RPE | 10 | 35% | 6.5 |
| Epidermis | 100 | 7% | 1.7 |

It can be seen that between 600 and 900 nm, the optical absorption in blood remains relatively low, while the absorption in the targeted pigmented tissues tapers-off monotonically. This is the preferred therapeutic window. Light in this region will be absorbed primarily in pigmented cells, and concentrated vasculature, while passing readily through partially bloody environments. Of course, in the case of PDT, the exogenous photoactivator is the intended absorber.

Figure 3:
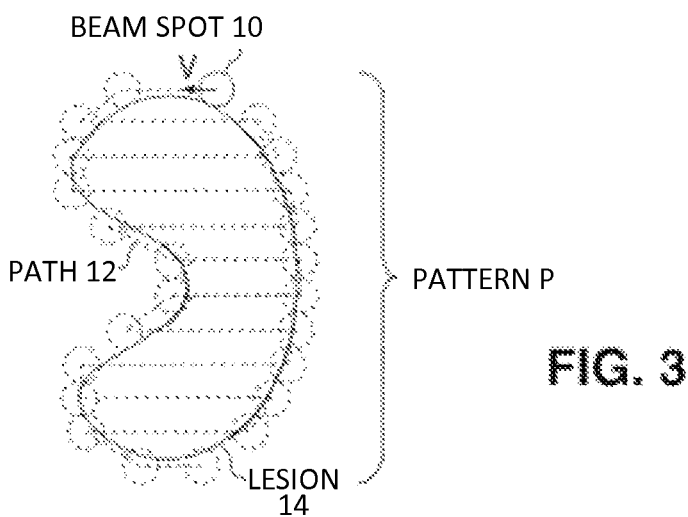
FIG. 3 is a schematic representation illustrating contiguous scanning of treatment light within the identified boundaries of a lesion.

FIG. 3 illustrates the scanning concept of the present invention. Instead of applying a single beam spot of light covering the entire lesion (and much of the surrounding tissue), a smaller beam spot of light 10 is contiguously scanned (traced) in a pattern P along a path 12 that covers the entire targeted lesion 14 with treatment light without unnecessarily exposing adjacent tissue. If the velocity V and power density of the beam spot 10 are constant, and a serpentine pattern that covers every portion of the lesion once is selected, then all portions of lesion 14 can be irradiated with a uniform dose of light. However, by using a beam spot 10 having a size significantly smaller than the lesion 14, the velocity V and/or power density of the beam spot 10 can be varied to provide varying irradiation to different portions of the same lesion. This would allow the overall integrated energy or heat generation and its subsequent temperature rise to be tailored to the particular clinical need. For example, when performing PC or TT, uniform energy density is not of primary concern, but the temperature elevation is. With that in mind, one may adjust the scan parameters (the spot size, the power density, the velocity of the beam spot, the path used, etc.) to provide more energy at the edges of a pattern P than at its center to create a more uniform temperature profile. The path 12 need not necessarily be the serpentine shape as shown in FIG. 3, but rather may take any shape that meets the clinical needs of the procedure. For example, a spiral-like path lends itself well to varying optical power between the center and edges of the pattern. When performing PDT, however, uniform energy density is critical.

Figure 4:
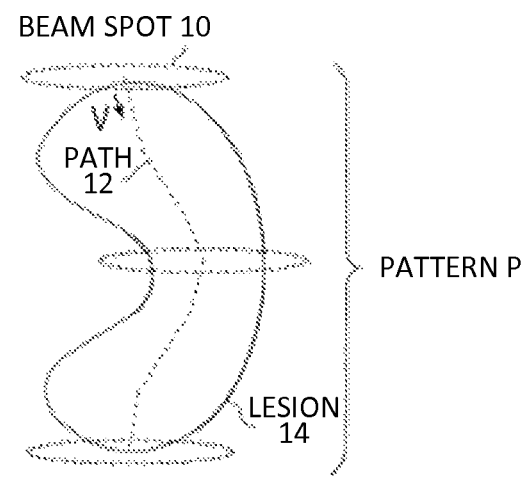
FIG. 4 is a schematic representation illustrating contiguous scanning within the identified boundaries of a lesion using an elongated treatment light spot.

It should be noted that beam spot 10 need not be round, and instead can be any shape that meets the particular clinical needs, such as uniform cumulative fluence or temperature rise across the target lesion 14. For example, FIG. 4 illustrates an elliptically shaped beam spot 10, with the path 12 extending along a meandering center line of the elongated lesion 14. An asymmetric beam spot may be scanned along its minor axis as shown, along its major axis, or even askew to either axis. The orientation and/or size can be varied during the scan, to better match the boundaries of the target lesion 14. In the context of FIG. 4, the length of the major axis of the beam spot 10 can be varied as the spot travels down the centerline path 12 to match the opposing boundaries of the lesion 14, yielding a very precise scan of lesion 14.

Figure 5:
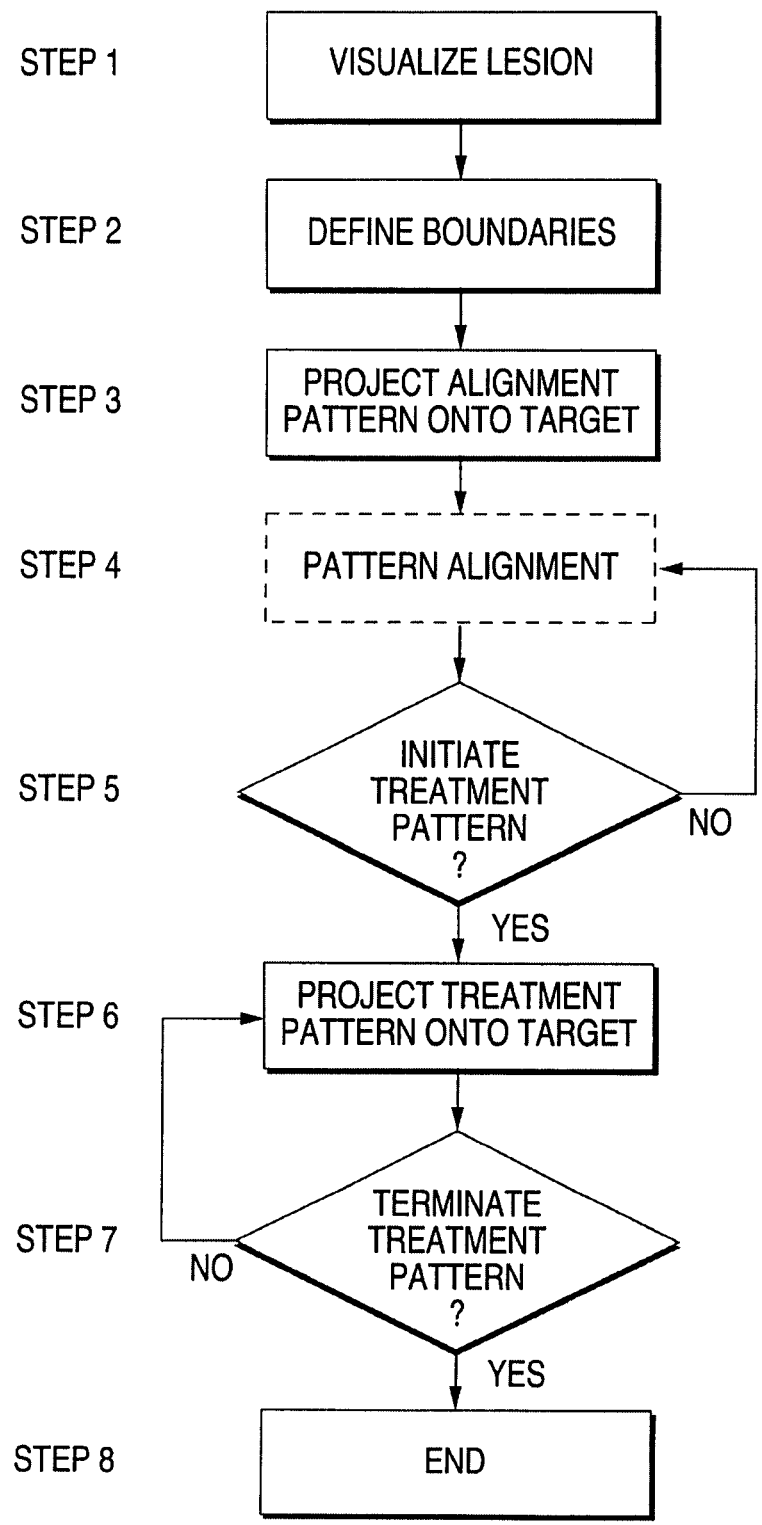
FIG. 5 shows a flow diagram illustrating the method identifying the boundaries of a lesion, aligning a treatment pattern to the identified boundaries, and projecting treatment light onto the lesion in the form of the treatment pattern.

FIG. 5 a flow diagram illustrating the 8-step method of scanning beam spot 10 along path 12 onto lesion 14. Step 1: visualize the target lesion. This may be done directly using instruments such as, but not limited to, a biomicroscope, an endoscope, a camera, or the naked eye. Once visualized, the image(s) of the lesion may be recorded. Step 2: define the boundaries of the target lesion 14. The boundaries, which may include the peripheral margins for simplicity) define an enclosed perimeter of the lesion. Boundaries may be defined, for instance, by outlining the target lesion manually, or by automatic means when the image of the target lesion is recorded. Such analysis may be done by software, or hardware. The exact manner of this image processing is highly dependent upon the specific clinical circumstances, as discussed in further detail below. Step 3: project a visible alignment pattern P onto the tissue containing the target lesion. Although this step is optional, projecting pattern P using an alignment beam that matches the pattern P of the eventual treatment beam spot 10 will help ensure the proper alignment of the treatment light onto the target tissue. Step 4: adjust the pattern P to match the target lesion and match the needs of the clinical procedure. Adjustments to the pattern P can include changes to the position, size, rotation and/or scale of the pattern, as well as changes to the size or shape of the beam spot itself. This adjustment is made relative to both the defined boundaries of the lesion as well as the clinical goals of the treatment (uniform exposure versus targeted and varying heating). If an alignment pattern is used, pattern adjustment can be implemented by adjusting pattern P so that every portion of the lesion within the defined boundaries is illuminated by the alignment pattern.

As described above, a typical photomedical treatment entails projecting an aiming beam directly onto the target tissue (e.g., a structure on or within a patient's eye) to generate an alignment pattern thereupon. A pattern can be one or more stationary or moving spots, or an image or shaped object scanned or otherwise created. A physician can see the projected alignment beam pattern on the patient's eye, and align this pattern to the desired target tissue thus aligning the treatment beam(s) which are coincident therewith. With this treatment method, the patient also sees the alignment beam pattern. The treatment/diagnosis described herein can employ an aiming device that is optically coupled primarily to the physician's eye and not the patient's eye. This is accomplished by generating a virtual alignment pattern that the physician can see and use to align the treatment beam(s), but without projecting the alignment pattern onto the target tissue. This can be done using a heads-up display in the observer's optical path. Thus, while the physician sees an image of the patient's eye shared with an alignment pattern superimposed thereon, the patient does not see the alignment pattern. Thus, the system can ideally achieve this sharing of the eye image with the alignment pattern by using a virtual alignment pattern located at an image plane that is conjugate to the targeted eye structure.

As used herein, a "real" alignment pattern is one in which alignment beam light is actually projected onto the target tissue, and which is subsequently scattered and/or reflected from the target tissue and viewed by the user. A "virtual" alignment pattern is one which the alignment beam light is superimposed onto the view of the target tissue but without projecting this alignment beam light onto the tissue itself. The virtual alignment pattern does not rely upon the interaction of the aiming beam light with the targeted tissue in order for the physician or user to obtain a view of the alignment pattern.

Once the location of pattern P is properly aligned to the lesion, Step 5 is performed: initiate treatment pattern projection onto the target tissue. This step is performed by an operator, such as by pressing a foot petal or finger trigger. If this step is not initiated, the system performing this method should return to Step 4, where the alignment pattern continues to be projected onto the target tissue to give the user the ability to align it to the target lesion. Step 6: project pattern of treatment light onto target tissue. Once treatment pattern projection is initiated, projection of the pattern onto the target issue is preferably performed automatically by the system performing this method. This step entails scanning the treatment light onto the lesion in the pattern P (that is substantially aligned to the alignment pattern if used). This treatment pattern P (along with the alignment pattern if used)

may be comprised of one or more contiguous scans, which are traced on the target tissue one or more times, depending upon the particular clinical need. The time taken to complete the scanning of the treatment pattern is preferably relatively short, to minimize the risk of significant movement between the pattern P and the target lesion. For example, in the case of retinal therapy, it can be difficult to maintain alignment between pattern P and the target tissue for more than about one second when using a contact lens. Therefore, for this type of therapy, the treatment pattern may need to be realigned after one second. In gastroenterology and dermatology, the alignment between the pattern P and target tissue can be maintained possibly for longer periods, and is largely limited by the stability of the delivery mechanism itself and any resting tremor. Periods for significant resting tremor of the hands have been measured to be on the order of 150 ms. Although, if relatively large margins are defined for the target lesion, then alignment of the treatment pattern becomes less of an immediate concern and the treatment pattern may be made to run substantially longer.

At some point during the treatment, Step 7 is performed: continue or terminate the application of treatment pattern. This step allows the user to continue scanning the treatment pattern and thus continuing therapy (e.g. by keeping a footswitch pressed) or terminating the treatment application. In the former case, the method reverts to Step 6 and continues projecting the treatment beam onto the target tissue. In the latter case (once it is determined that that the treatment should be ceased), Step 8 is performed: terminate the treatment procedure.

It should be noted that this method is independent of the light source(s) used, and thus this method is broadly applicable to the use of cw, or quasi-cw light sources for PC, PDT, and TT. It should also be noted that the alignment pattern (if used) need not be identical to the treatment pattern P, but instead could be a pattern that defines the boundaries of the treatment pattern P in order to assure that the treatment beam is delivered only within the desired area for patient safety. This may be done, for example, by having the alignment pattern provide an outline of the intended treatment pattern. In this way the spatial extent of the treatment pattern may be made known to the user (as opposed to the exact locations of spot 10 as it traverses path 12), where the user simply aligns the alignment outline to the defined boundaries of the targeted lesion. The alignment pattern may also be made to be perceived as blinking in order to further enhance its visibility to the user.

Figure 6:
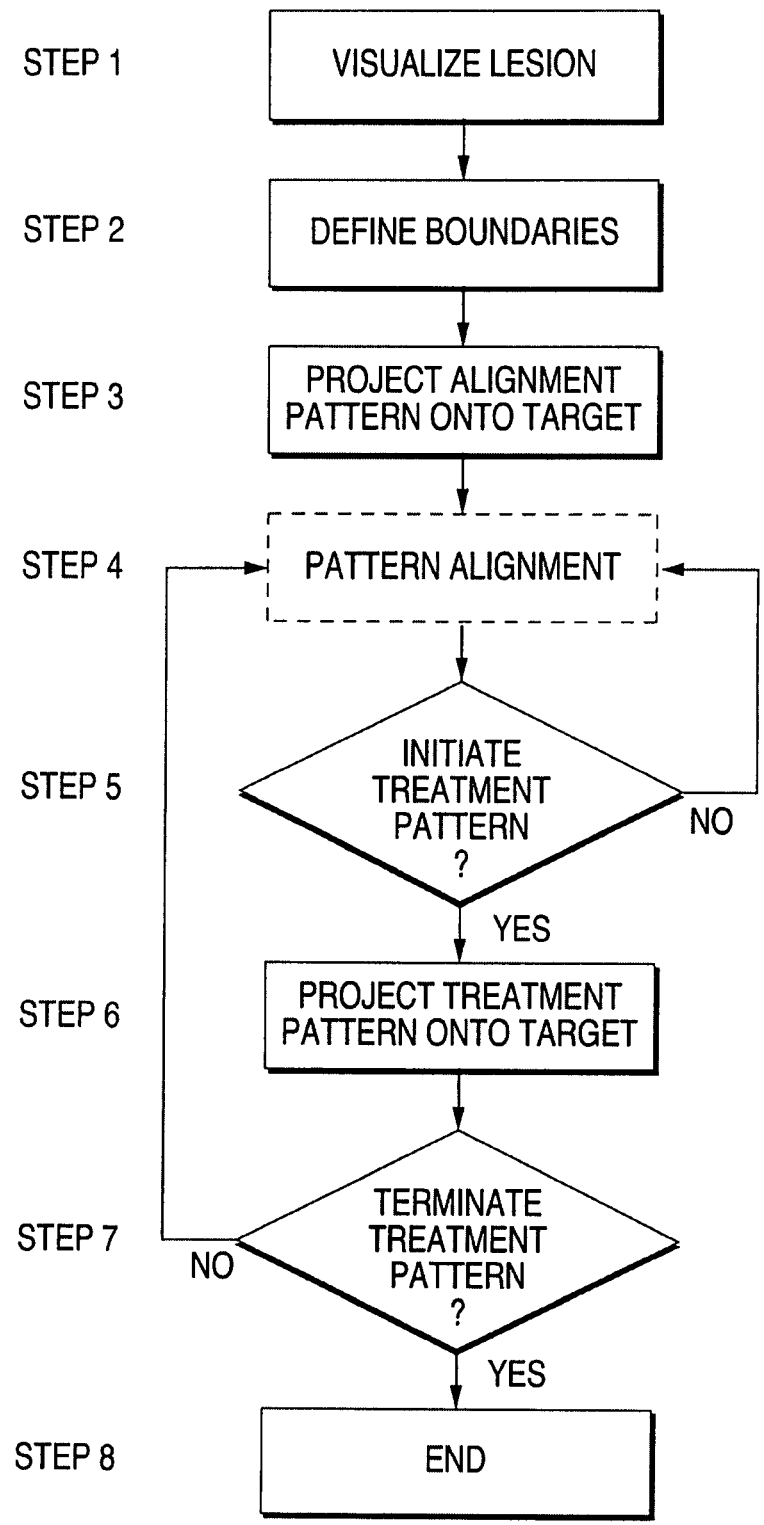
FIGS. 6-7 are flow diagrams illustrating alternate embodiments to the method of FIG. 5.

FIG. 6 a flow diagram illustrating an alternate method similar to that of FIG. 5. The method steps in FIG. 6 are the same as those in FIG. 5, except that once it is determined in Step 7 that the treatment pattern projection should terminate, the method reverts back to Step 4 to allow the operator to realign the patterns, rather than simply terminating the procedure (i.e. if for example there is excessive motion between the target lesion and the treatment pattern). Step 7 allows the user to continue scanning the treatment pattern, thus continuing therapy, for example, by keeping a footswitch pressed, or to realign the pattern. This may be done during administration of the treatment pattern, or it might be made to wait for user input prior to proceeding. This latter case would likely only be done in the case where the boundaries are not defined automatically and/or there is relatively large motion between the target lesion and the scanned patterns.

Figure 7:
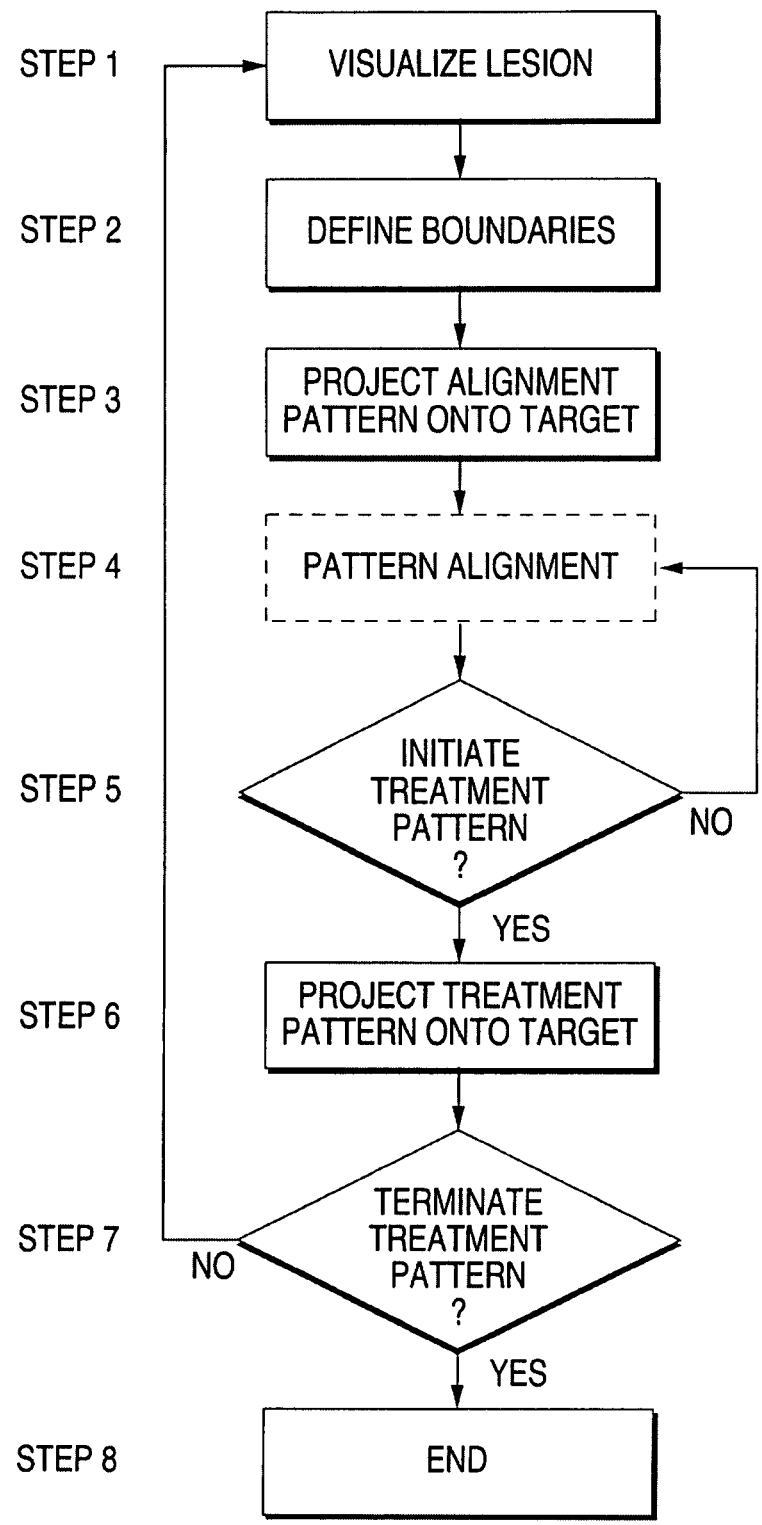

FIG. 7 a flow diagram illustrating another alternate method similar to that of FIG. 5. The method steps in FIG. 7 are the same as those in FIG. 5, except that once it is determined in Step 7 that the treatment pattern projection should terminate, the method reverts back to Step 1, where lesion visualization takes place again. This allows an implementing system to automatically realign the patterns to the lesion, rather than having the user do so.

FIGS. 8-17 illustrate various system embodiments for implementing the treatment methods described above. With respect to FIG. 8, it illustrates the components of a system suitable for treating target tissue as outlined above. The system 20 includes a light source 22 for generating the treatment beam of light 24. Exemplary light sources includes gas, solid state, and diode laser devices, flash lamps, light emitting diodes, etc. A scanner 26 is used to deflect the beam into a pattern P. Light source 22 and/or scanner 26 can be controlled by control electronics (i.e. a controller) 28 via input and output device 30. Controller 28 may be a standard computer running software, or can be dedicated computing device such as a microprocessor coupled to memory. The position and character of pattern P may be further controlled by the user via an input device 32 (e.g. such as a joystick or mouse), and/or a graphic user interface (GUI) 34. The scanned treatment beam 24 eventually traces out pattern P on the targeted lesion 14 contained in target tissue 16. The actual tracing of beam 24 on the target tissue is not only dictated by the optics of system 20, but also patient idiosyncrasies that might serve to perturb beam 24, such as cataracts, retinal inhomogeneities, intraocular debris, and gross surface roughness. The target tissue is visualized by the user either by the naked eye, or by a visualization device 36 such as, but not limited to, a camera, biomicroscope, fundus camera, SLO, or OCT system. The output of visualization device 36 may be observed directly, or displayed on a screen or the GUI 34 for simplified control of the system. The output of visualization device 36 may also be sent to controller 28, which can automatically visualize the lesion and define its boundaries.

There are numerous possible approaches for detecting the boundaries of a lesion. The simplest technique involves the observer indicating the boundaries themselves manually, which would preferably involve the user using the GUI 34 to input to the system the boundary locations observed by the user. Another technique is to have an image processor integrated into the control architecture of the system. In such a configuration, one may choose to exploit morphological or rank filtering to identify the lesion boundary. Examples of such possible approaches include, but are not limited to; blob analysis, matched filters, edge detection schemes, etc. These schemes often involve a spatial convolution operation and can be computationally intensive. An often more expeditious approach would be to operate in the frequency plane via the use of FFTs, etc. Still other boundary detection techniques are disclosed in U.S. Pat. Nos. 4,538,299 and 5,625,709, which are incorporated herein by reference.

In order to register the location of the lesion within the available scan field, the scan field should first be co-registered with the visual field. This can be done a number of different ways. For example, a card can be placed in the visualization image plane containing a pattern of known size and shape. The scanner would then be set to trace the pattern and thereby register the scan and visual fields. From this point on, these systems are co-registered regardless of changes to the object observed.

Similarly, when virtual alignment means are used, this system may also be co-registered by using targets. Alternately, one may project a virtual pattern, and tune the scanner to describe the virtual pattern, which registers the virtual alignment system. In this manner, the scanning system may be made to dispose a beam within the identified boundaries of a lesion.

Scanner 26 can include one or more optical elements that deflect the treatment beam 24 produced by the light source 22 (for example by reflection, refraction, or acousto-optic deflection). One simple example of such optical elements would be two mirrors that rotate in orthogonal directions. Other beam deflecting optical elements can include rotating wedges, translating lenses, translating mirrors that have a surface curvature (optical power), moving gratings, a two dimensional acousto-optic deflector, or even an adaptive optic such as an optical phased array. In the case where an optical element has optical power, compensating optical elements (not shown) may be required to produce an image, as opposed to a simple illumination. In operation, system 20 can automatically or semi-automatically visualize the legion 14, determine the locations of its boundaries, and generate a pattern of treatment light that is traced along the interior of the lesion without unduly exposing adjacent, non-lesion tissue (e.g. as illustrated in FIGS. 3 and 4).

Figure 8:
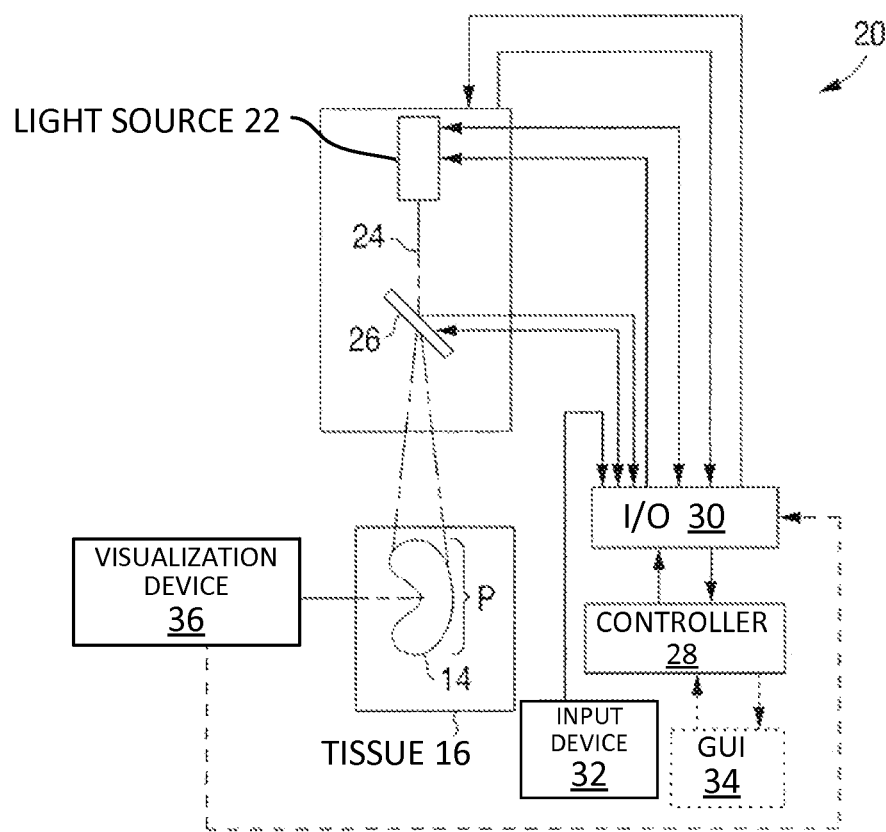
FIG. 8 is a schematic representation of a system for identifying the boundaries of a lesion, aligning a treatment pattern to the identified boundaries, and projecting treatment light onto the lesion in the form of the treatment pattern.
Figure 9:
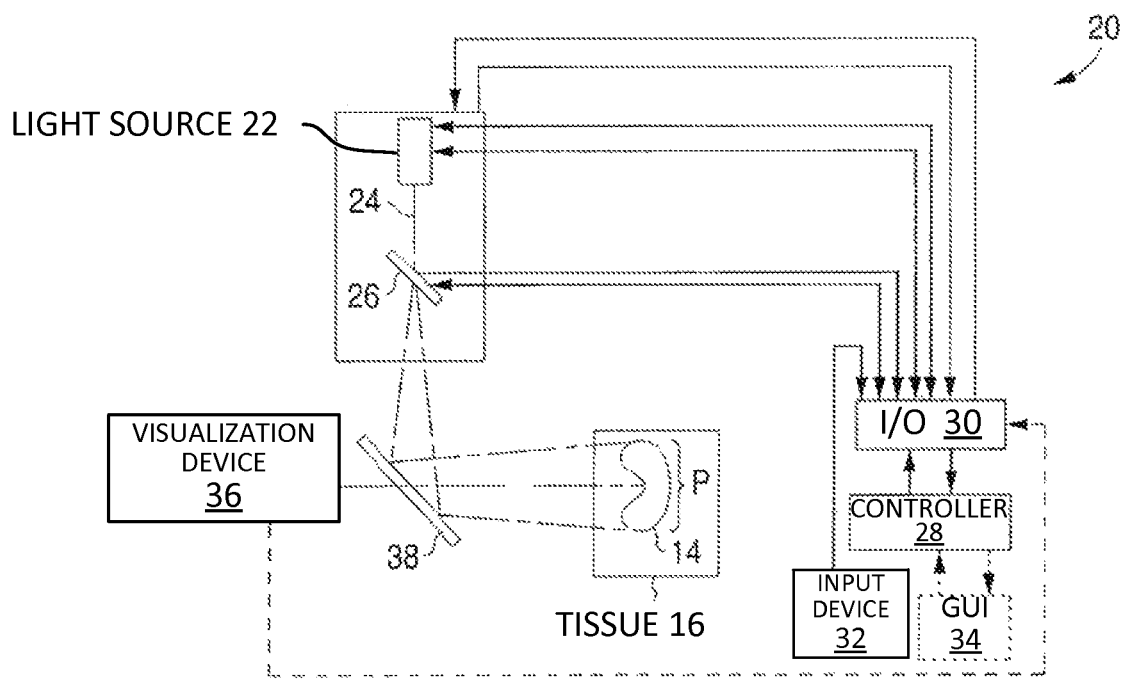
FIGS. 9-17 are schematic representations of alternate embodiments of the system of FIG. 8.

FIG. 9 illustrates an alternate embodiment of system 20 similar to that shown in FIG. 8, but with a mirror 38 that is used to redirect the treatment beam 24 toward the target tissue. Visualization device 36 visualizes the target tissue through mirror 38. The size of mirror 38 may be minimized in an attempt to increase the overall solid angle subtended by the visualization device 36. When mirror 38 is small, it may be placed directly in the visualization path without much disturbance. It may also be placed in the center of a binocular imaging apparatus, such as a slit-lamp biomicroscope, without disturbing the visualization. Mirror 38 may also be made large enough to contain the entire scan, and could be formed as a high reflector spectrally matched to the output of light source 22 alone with visualization accomplished by looking through mirror 38. A further refinement could be to white balance the transmission of mirror 38 by using a more complicated optical coating to make the colors in the visualization of the target tissue appear more natural.

Figure 10:
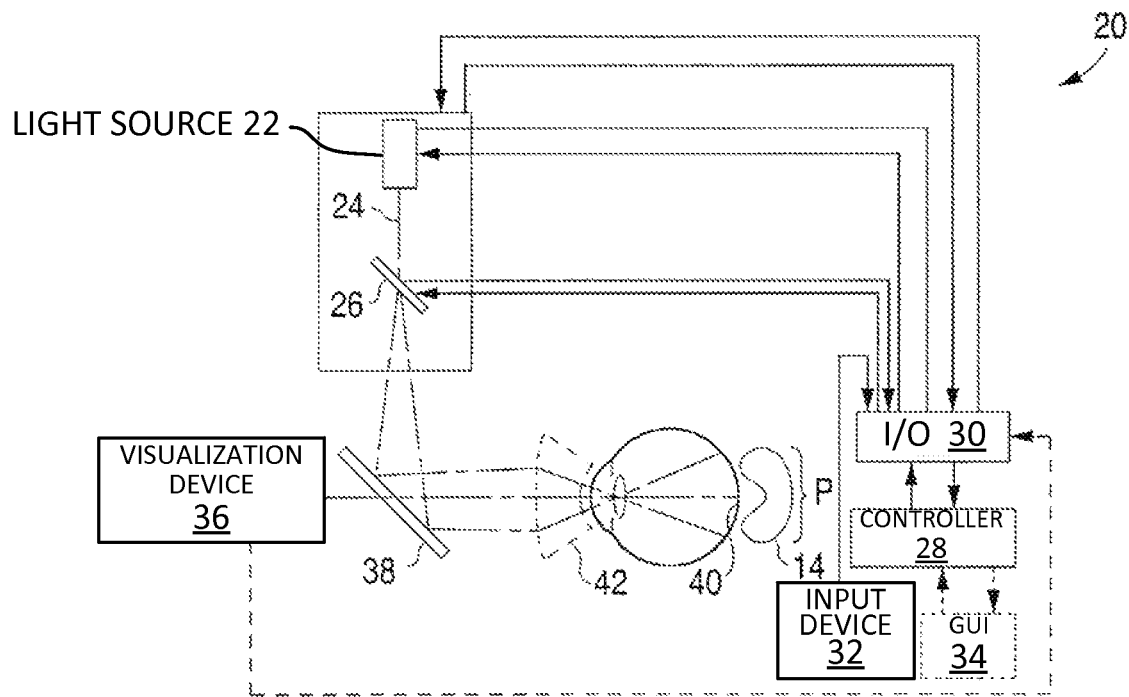

FIG. 10 illustrates an ophthalmic application of the embodiment of system 20 shown in FIG. 9. Here the target lesion 14 is contained on a patient's retina 40. An ophthalmic contact lens 42 placed in contact with the patient's eye is used to focus the treatment beam pattern P onto the retinal lesion 14, and to provide visualization of the retinal tissue. The contact lens 42 also serves to partially restrain movement of the patient's eye, thus increasing the time in which the treatment scan can take place.

Figure 11:
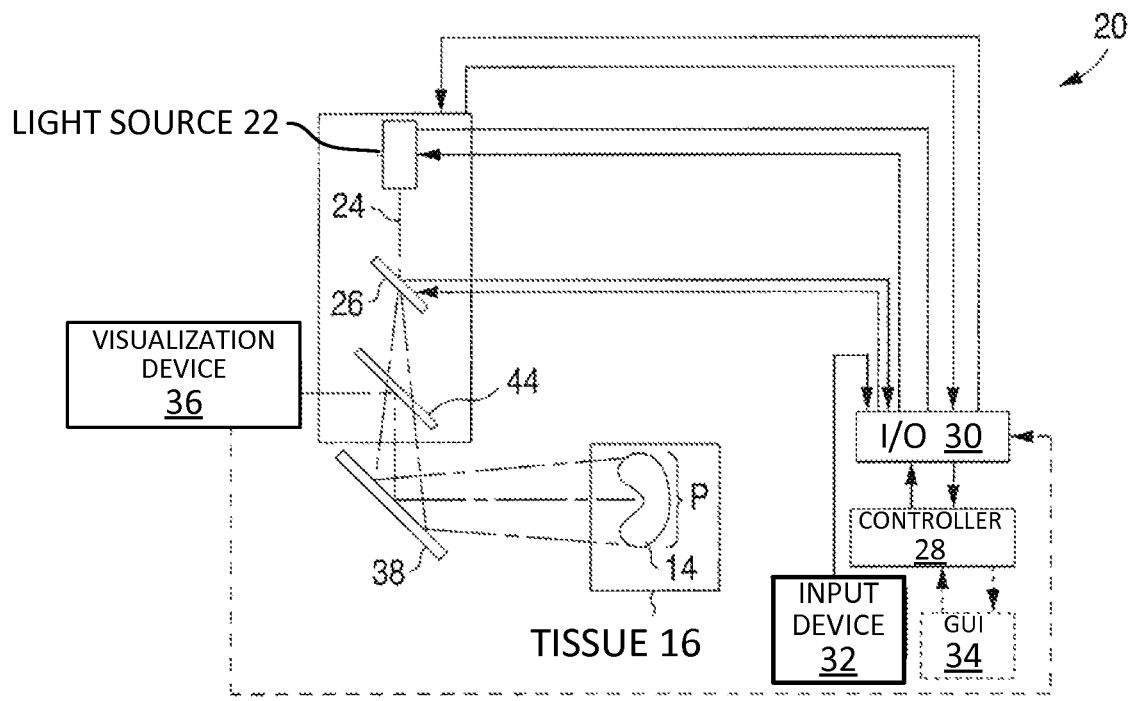

FIG. 11 illustrates an alternate embodiment of system 20 similar to that shown in FIG. 10, but with the addition of an additional mirror 44 that is used to direct light from the target tissue to the visualization device 36. Mirror 44 allows for the visualization device 36 to be placed arbitrarily in the system, rather than being forced to be behind mirror 38.

Figure 12:
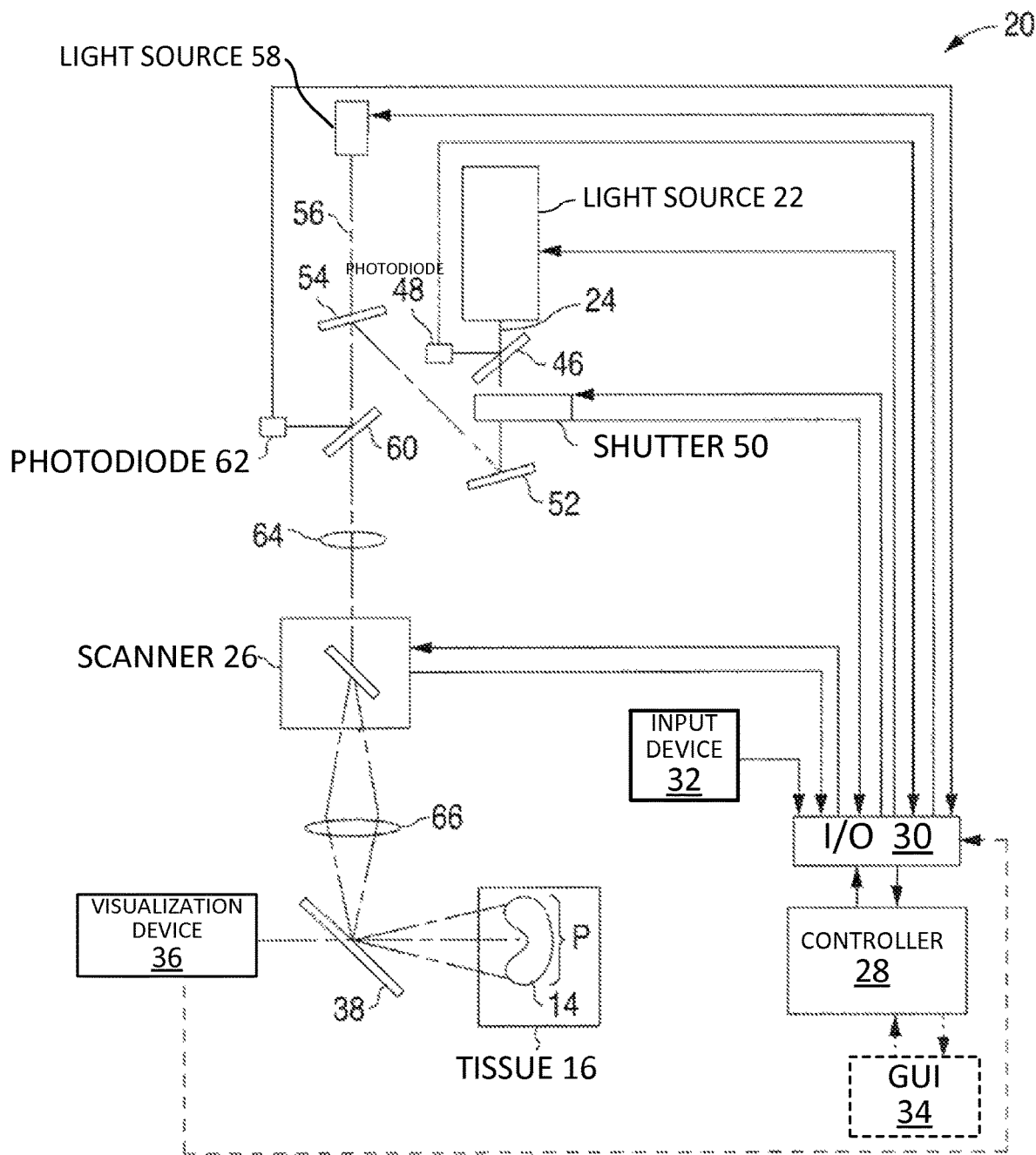

FIG. 12 illustrates an alternate embodiment of system 20 similar to that shown in FIG. 10, but with the addition of several components so that the system can produce both alignment patterns and treatment patterns. In this embodiment, treatment beam 24 leaving light source 22 first encounters mirror 46 which serves to reflect a fixed portion of treatment light towards a photodiode 48 for measuring the power of the treatment beam 24. Treatment beam 24 then encounters a shutter 50 that selectively blocks treatment beam 24. Mirror 52 then directs beam 24 to mirror 54, which is a combining mirror that combines treatment beam 24 with an alignment beam 56 from an alignment light source 58, so that alignment light and treatment light propagate along the same optical path. Having alignment beam 56 co-linear with treatment beam 24 means that the location of alignment beam 56 on the target tissue will visually indicate where the treatment beam 24 will be incident on the target tissue. Mirror 60 and photodiode 62 serve purposes similar to those of mirror 46 and photodiode 48, and additionally allows for a redundant monitor of the state of shutter 50. Lens 64 may be provided to condition light beams 24, 56 as they enter the scanner 26. Lens 64 may be a single lens element or a compound lens. Another lens 66 may be provided to condition light beams 24, 56 exiting scanner 26. Lenses 64, 66 can dictate the cross-sectional size and/or shape of the beams 24, 56. If lens 66 is placed one focal length away from the optical midpoint of scanner 26, then a telecentric scan can result, which serves to maximize the scan speed. In the case of a telecentric scan configuration, mirror 38 would need to be large enough to contain the entire scan, and could be made a reflector spectrally matched to the outputs of light sources 22, 58, while still allowing visualization therethrough from the target tissue.

In practice, and under the control of controller 28, alignment source 58 is first activated to show the user the disposition of the pattern P on the target tissue, and to allow the user to adjust the pattern and its location for proper alignment it to lesion 14. Once the desired alignment is achieved and/or verified, then the treatment light source 22 is activated to project pattern P of treatment beam 24 onto the lesion 14. Preferably, alignment beam 56 is visible to the naked eye. However, if a visualization scheme is used that is sensitive to non-visible light, such as infrared imaging, then light outside the visible range can be used for alignment beam 56.

Figure 13:
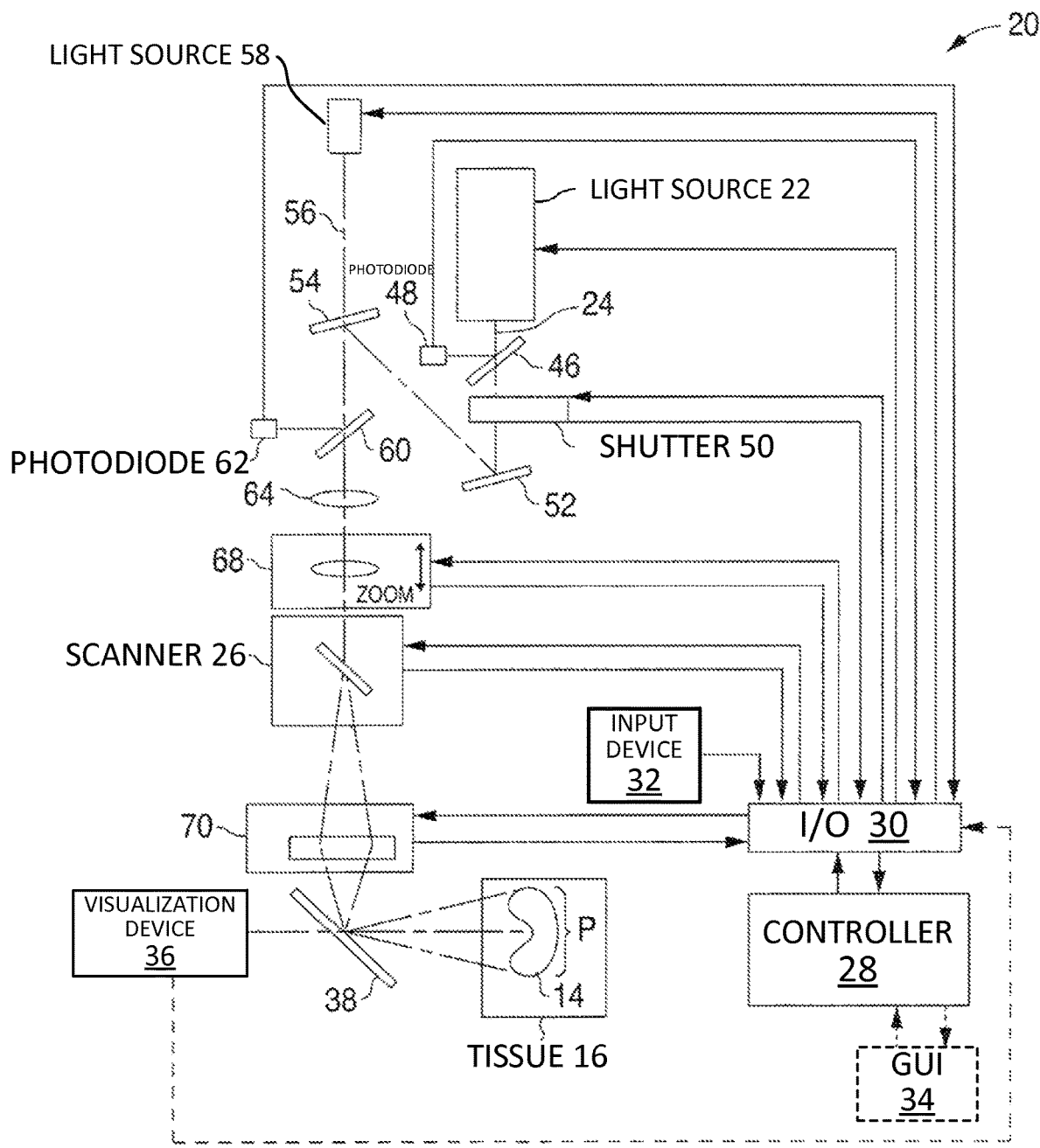

FIG. 13 illustrates an alternate embodiment of system 20 similar to that shown in FIG. 12, but with the addition of movable lens 68. Lens 68 is movable toward and away from lens 64 to adjust the size of the beams 24, 56 that make up pattern P, and thus adjust the size of pattern P itself. In addition to, or alternative to, lens 68 (which is disposed before scanner 26), a movable lens 70 disposed after scanner 26 (in place of lens 66) may be used to dynamically adjust the size (and/or shape) of both the beams 24, 56 as well as the pattern P generated by scanner 26 using these beams. Lenses 68 and 70 may or may not be anomorphic, and could include several optical elements in the form of a telescope system or compound toroidal lens. The beam and pattern size adjustments allow the system to match the size of pattern P, and beams 24, 56 forming the pattern P, to the target lesion 14.

Figure 14:
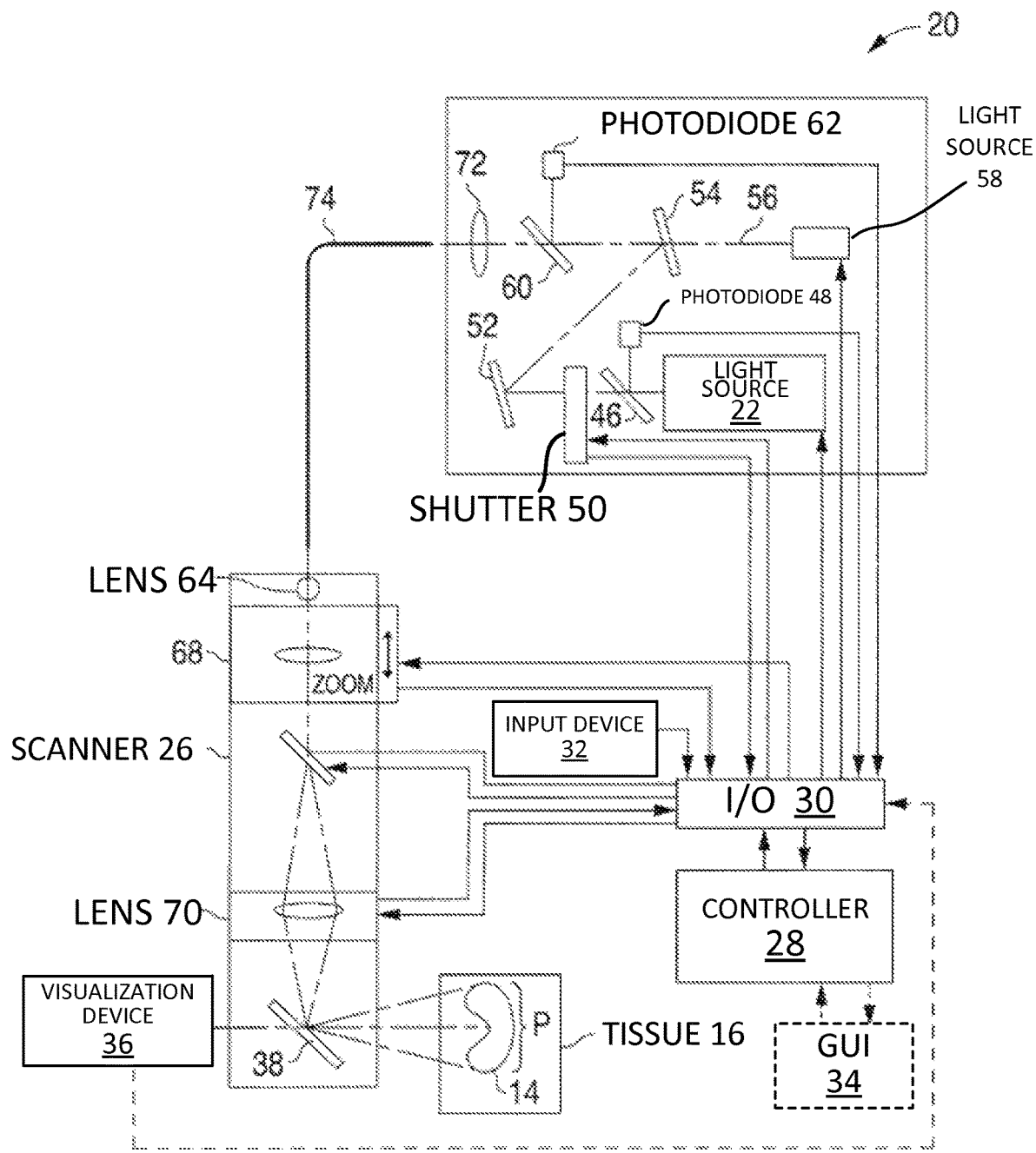

FIG. 14 illustrates an alternate embodiment of system 20 similar to that shown in FIG. 13, but with the light sources 22, 58 separated from the scanner 26 and size adjusting lenses 68, 70 using an optical fiber. Specifically, a lens 72 is used to inject beams 24, 56 into an optical fiber 74. Light exiting optical fiber 74 encounters lenses 64 and 68 which condition the light (for proper pattern and beam size) prior to entry into scanner 26. Furthermore, an image of the output face of the optical fiber 74 may be relayed to the treatment area and a "flat-top" intensity profile used, rather than the typical Gaussian profile.

Figure 15:
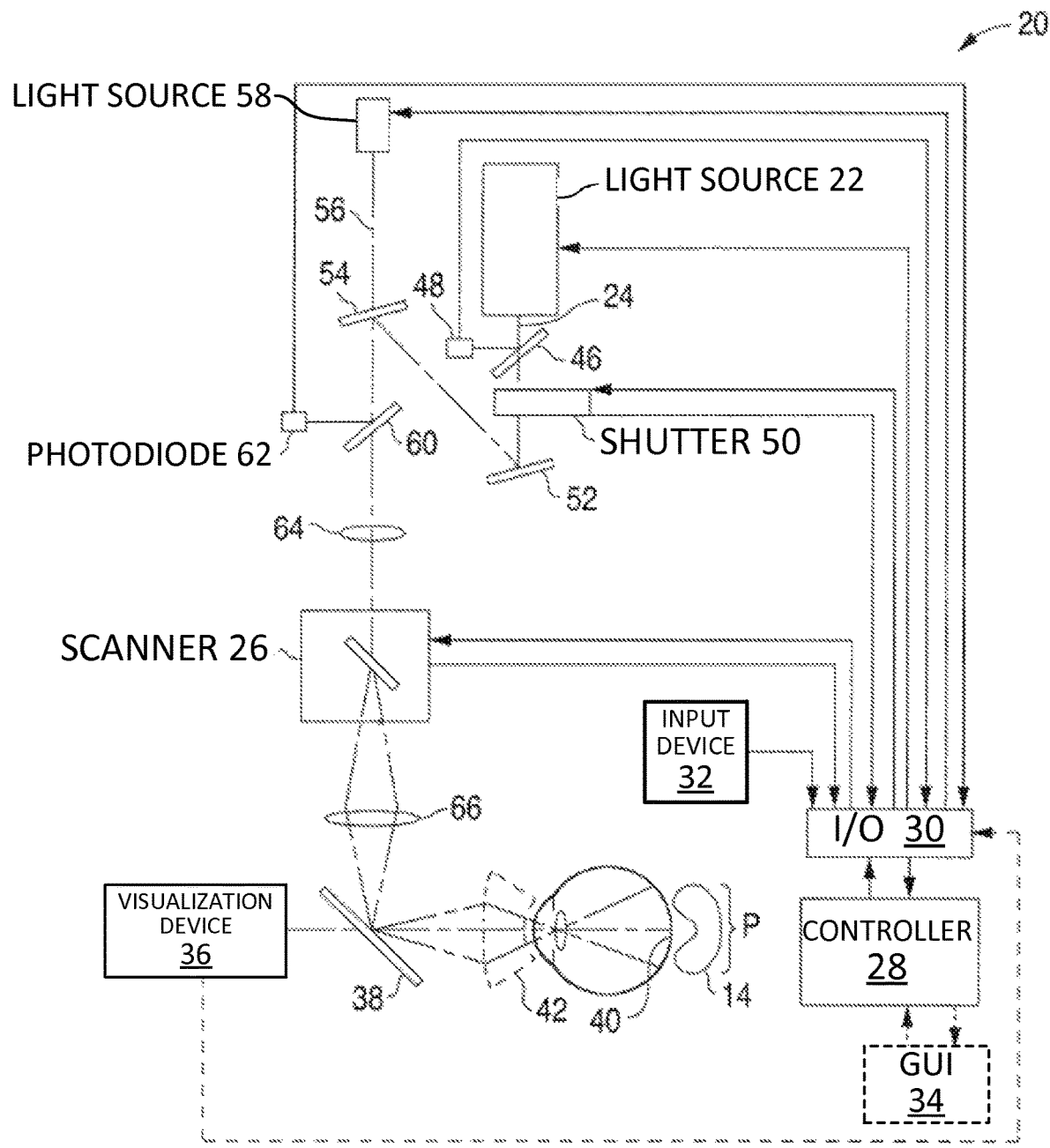
Figure 16:
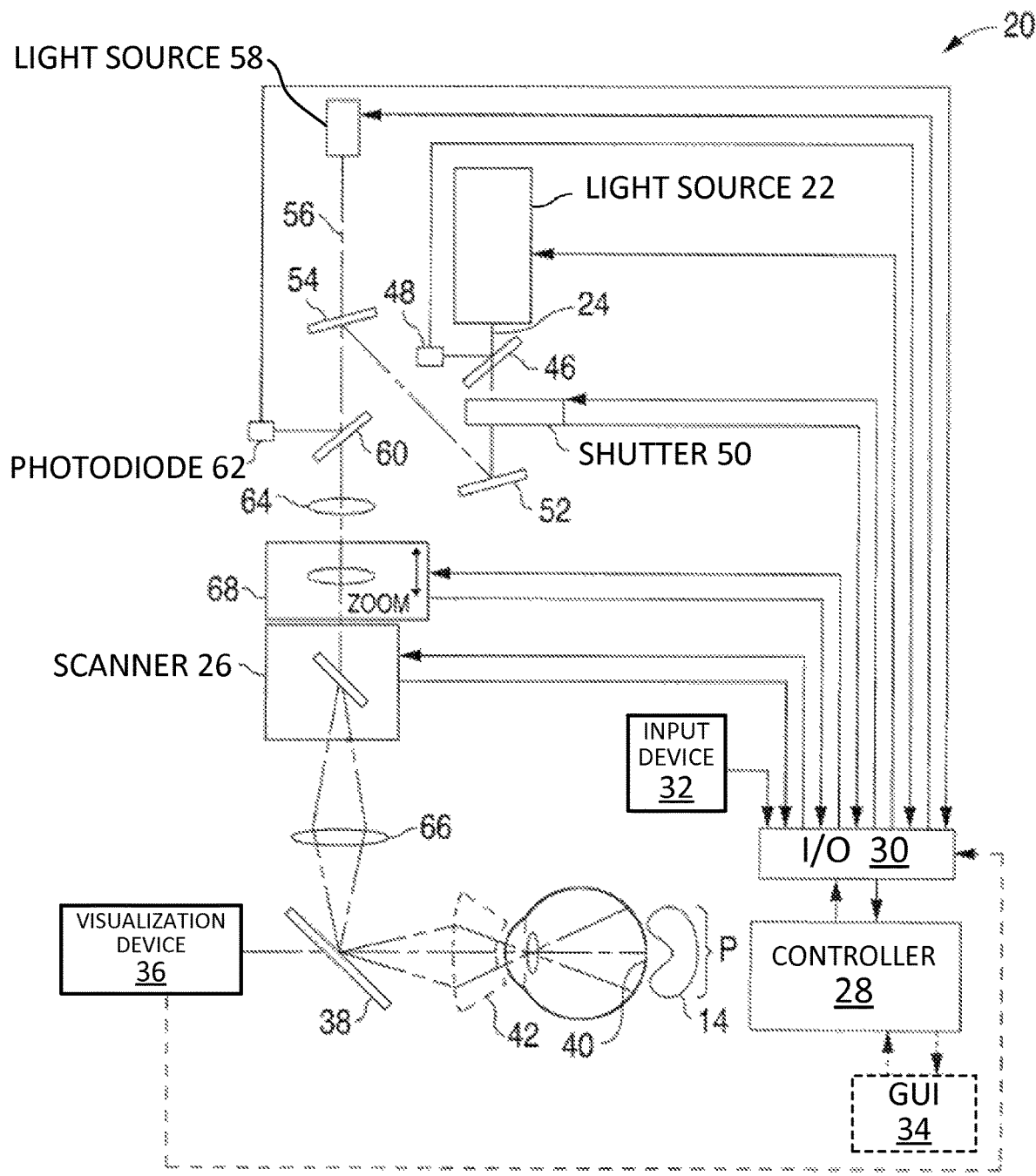
Figure 17:
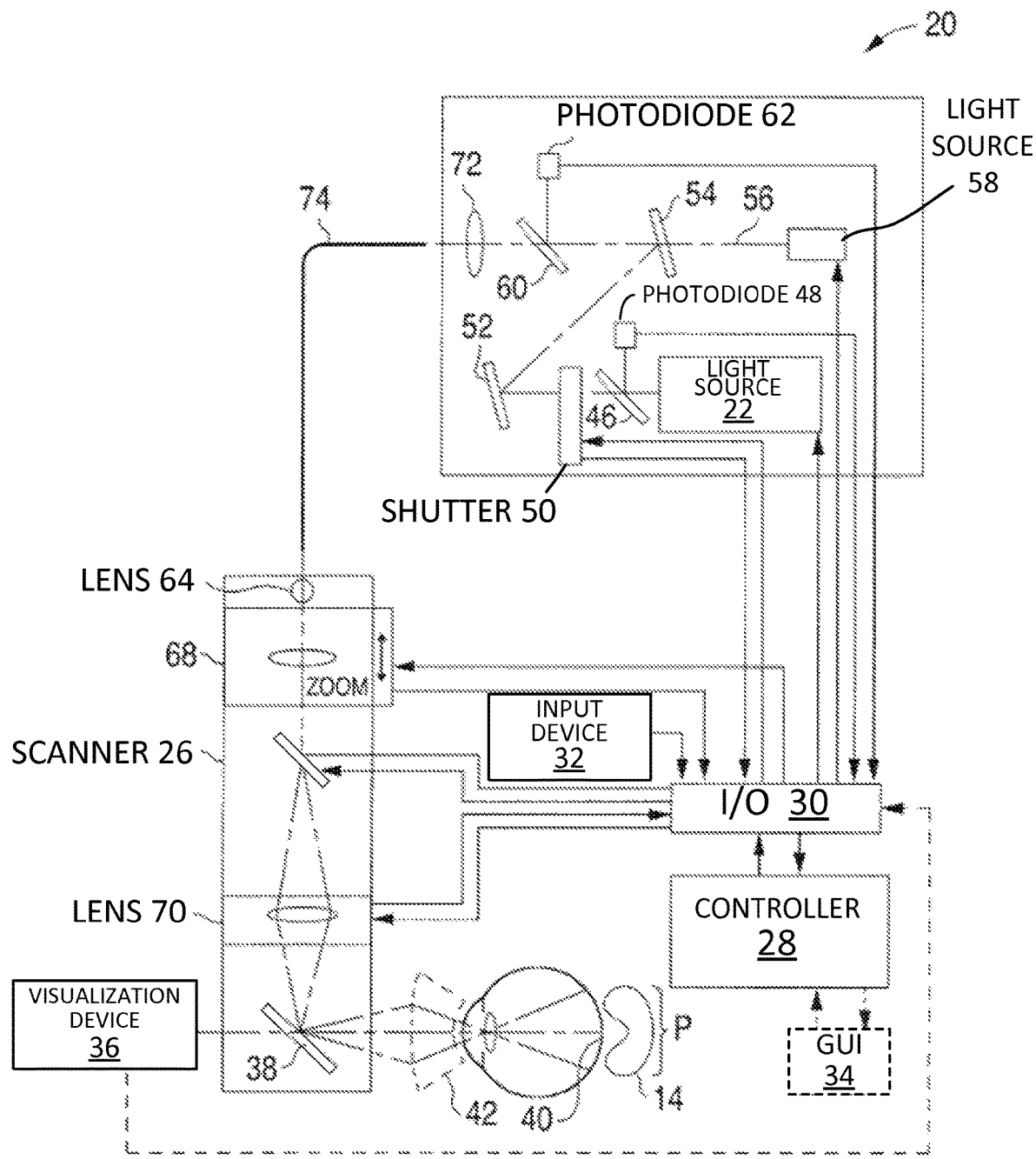

FIGS. 15-17 show the same system configurations as FIGS. 12-14, respectively, but as applied in an ophthalmic application using a contact lens 42 to apply the alignment and treatment patterns P to lesion 14 on the patient's retina 40.

The system configurations described above allow for contiguous scans with dynamic changes to the size and shape of both the beams and pattern P, to the scan direction, and to the power density, all tailored to the shape and size of the target lesion as well as the desired clinical effect of the treatment. Using a dedicated scanning mechanism to continuously move the beam to treat the lesion provides a multiplicity of advantages over simple fixed spot and raster scan approaches. Contiguous scanning with dynamic parameter adjustability provides for overall uniform cumulative energy deposition. The overall dosimetry of the treatment may be adjusted, for example, by tailoring the optical power in conjunction with the scan rate. When treating around the corners of a lesion, the beam naturally slows as it changes direction. When this happens, the optical power may be commensurately decreased in order to keep the integrated fluence constant. Likewise, the cumulative optical deposition may be tailored to provide a specified temperature profile. The intensity profile of the beam spot on the target tissue (e.g. Gaussian, flat-top, etc.) should be considered, but the inherent flexibility of the present invention accommodates a wide variety of such beam profiles by adjusting the nesting nature of adjacent scans. As such, it is not limited to any specific beam profile, and works equally well for all profiles. For example, to achieve a reasonable level of cumulative uniformity, adjacent scan paths of a flat-top beam will not be placed as close together as those of a Gaussian beam of the same size. Lastly, the contiguous scans can follow the projection of an alignment pattern so that the user has a real-time visual indicator of the intended treatment pattern size and location.

Figure 18:
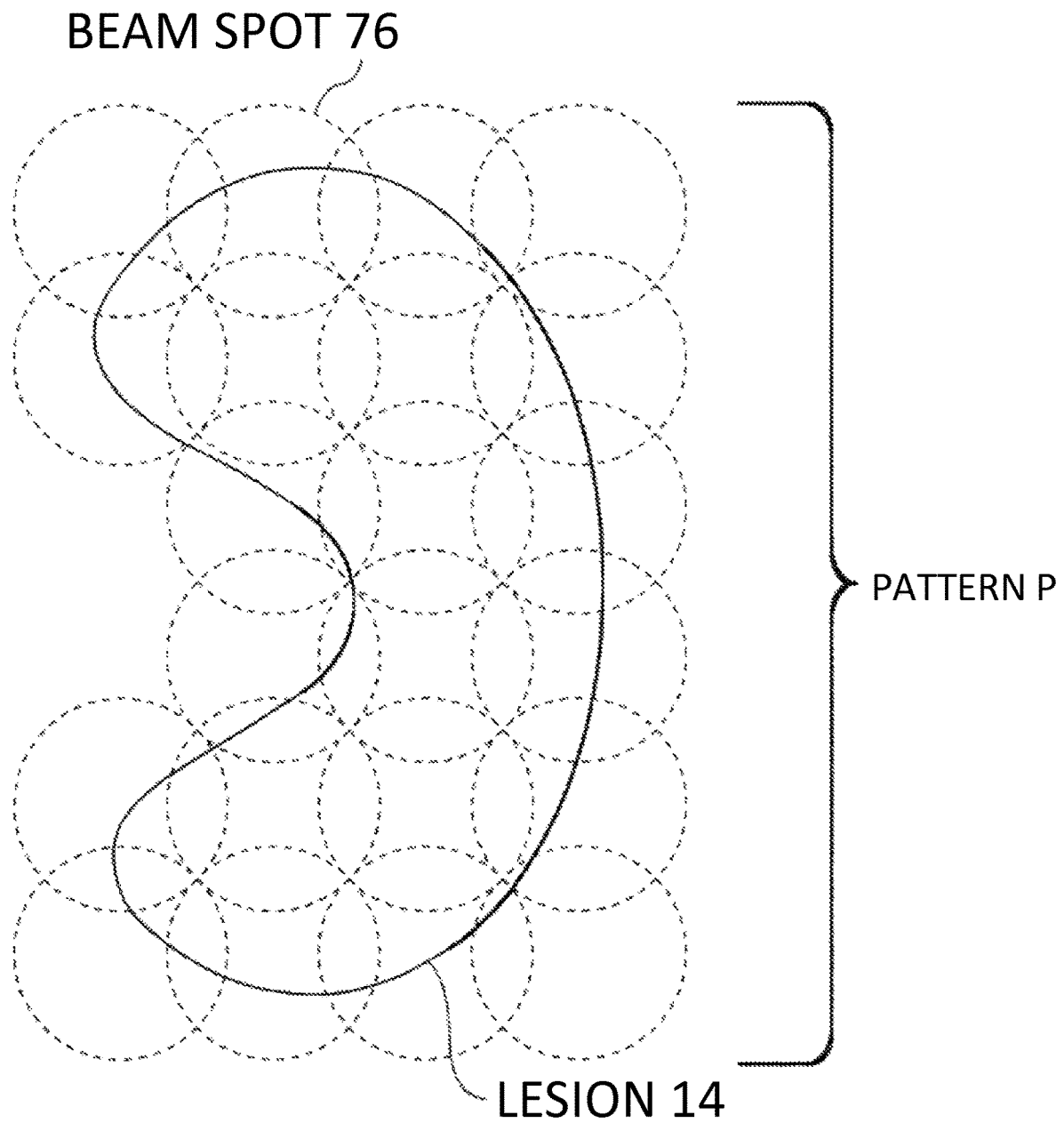
FIG. 18 is a schematic representation illustrating an alternate technique for scanning treatment light within the identified boundaries of a lesion.

While contiguous scanning of cw and quasi-cw light sources have the advantages disclosed above, even non-contiguous scanning provides beneficial results once the system visualizes the lesion and defines its boundaries. Specifically, in any of the embodiments described above, the light sources 22, 58 and/or shutter 50 can be operated to produce treatment and alignment beams 14, 56 that are pulsed. In this case, the scanner can be operated to move the beams between pulses, but be stationary as the light pulses are produced. In this case, pattern P is no longer a contiguous tracing of a continuous beam spot, but rather a plurality of discrete, stationary, and sequentially delivered spots of light 76 on the lesion, as illustrated in FIG. 18. These individual spots of light 76 (either treatment light, alignment light, or both) are confluent, approximating the shape of the lesion. The smaller the spot size, the better the fit. The amount of overlap shown assumes a Gaussian intensity profile for the fundamental spot. Other intensity profiles are, of course, possible, and so is the amount of overlap. In this example, spots 76 are delivered to the target tissue so long as there is more than an insignificant overlap between the spot location and portions of the target tissue at or inside the lesion boundaries.

It is to be understood that the present invention is not limited to the embodiment(s) described above and illustrated herein, but encompasses any and all variations falling within the scope of the appended claims. For example, the alignment beam could be generated by the same light source as the treatment beam (e.g. the light source has two distinct outputs, or the alignment beam is simply a much lower power version of treatment beam. While scanner 26 is shown and described above as optical elements that deflect the treatment and alignment beams 24, 56 after they leave light sources 22, 58, scanner 26 could be a translating and/or tilting device (e.g. such as a galvanometer, motor, or piezo-electric device) that translates and/or tilts the light sources 22, 58 themselves to deflect the beams 24, 56 exiting therefrom into pattern P.

What is claimed is:

1. A method for treating a lesion on target eye tissue, comprising:
capturing an image of target eye tissue containing an existing lesion;
generating a treatment light beam;
determining, by a computer processor, boundaries of the existing lesion, wherein the computer processor automatically determines the boundaries of the existing lesion from the captured image;
determining, by the computer processor, a treatment pattern based on the determined boundaries of the existing lesion of the target eye tissue, wherein determining the treatment pattern includes determining, by the computer processor, a geometry of the treatment pattern in accordance with a geometry of the determined boundaries of the existing lesion;
deflecting the treatment light beam in the form of the treatment pattern; and
projecting the treatment pattern onto the target eye tissue and within the determined boundaries of the existing lesion of the target eye tissue, wherein projecting the treatment pattern onto the target eye tissue comprises:
projecting the light beam onto the target eye tissue as a spot of light; and
scanning the spot of light along a path that forms the treatment pattern on the target eye tissue.

2. The method of claim 1, wherein the treatment pattern is a contiguous pattern.

3. The method of claim 2, further comprising:
selecting the path and a size of the spot of light for the treatment pattern such that the treatment light evenly irradiates an interior of the lesion defined by the determined boundaries with a uniform dose of light.

4. The method of claim 2, further comprising:
selecting the path and a size of the spot of light such that the treatment pattern generates a predetermined temperature profile in an interior of the lesion defined by the determined boundaries.

5. The method of claim 2, wherein the treatment light beam is cw or quasi-cw.

6. The method of claim 1, wherein the treatment light beam consists of non-visible light.

7. The method of claim 1, wherein the treatment pattern comprises discrete and overlapping spots.

8. The method of claim 1, further comprising:
generating an alignment light beam;
deflecting the alignment light beam in the form of an alignment pattern; and
projecting the alignment pattern onto the target eye tissue to visually indicate a position of the treatment pattern on the target eye tissue.

9. The method of claim 8, further comprising:
adjusting the position of the treatment pattern on the target eye tissue as indicated by the alignment pattern.

10. The method of claim 8, wherein the alignment pattern and the treatment pattern are identical and superimposed onto the same position on the target eye tissue.

11. The method of claim 8, wherein the alignment pattern encircles a portion of the target eye tissue in which the treatment pattern is contained.

12. The method of claim 1, further comprising:
generating a virtual alignment pattern for visually indicating a position of the treatment pattern on the target eye tissue.

13. The method of claim 1, further comprising:
adjusting a size of the treatment light beam on the target eye tissue.

14. The method of claim 1, further comprising:
adjusting a shape of the treatment light beam on the target eye tissue.

15. The method of claim 1, further comprising:
adjusting a size of the treatment pattern on the target eye tissue.

16. The method of claim 1, further comprising:
displaying the image of the target eye tissue.

17. The method of claim 1, wherein a scanning velocity of the spot of light decreases as the spot of light overlaps a portion of the determined boundaries of the existing lesion of the target eye tissue.

18. The method of claim 17, wherein an optical power of the spot of light decreases as the scanning velocity of the spot of light decreases.

* * * * *

UNITED STATES PATENT AND TRADEMARK OFFICE
CERTIFICATE OF CORRECTION

PATENT NO. : 10,617,564 B1
APPLICATION NO. : 11/800939
DATED : April 14, 2020
INVENTOR(S) : Dan Andersen et al.

Page 1 of 1

It is certified that error appears in the above-identified patent and that said Letters Patent is hereby corrected as shown below:

On the Title Page

Item (73), under Assignee, please delete "Apple Inc. (Cupertino, CA)" and insert --TOPCON MEDICAL LASER SYSTEMS INC. (Santa Clara, CA)-- therefor.

Signed and Sealed this
Seventh Day of July, 2020

Andrei Iancu
*Director of the United States Patent and Trademark Office*